United States Patent

Pengilly et al.

[11] Patent Number: 5,879,413
[45] Date of Patent: Mar. 9, 1999

[54] CATIONIC DIAZO DYES FOR THE DYEING OF HAIR

[75] Inventors: Roger W. Pengilly, Kings Lynn; Francis C. P. McLoughlin, Wisbech; Roger G. J. C. Twigg, Kings Lynn, all of United Kingdom

[73] Assignee: Warner-Jenkinson Europe Limited, Norfolk, United Kingdom

[21] Appl. No.: 980,028

[22] Filed: Nov. 26, 1997

[30] Foreign Application Priority Data

Nov. 27, 1996 [GB] United Kingdom ............... 9624590

[51] Int. Cl.⁶ ............... A61K 7/13; C07C 245/08; C09B 44/02
[52] U.S. Cl. ............... 8/426; 8/405; 8/662; 534/603; 534/580; 534/859
[58] Field of Search ............... 8/405, 426, 662; 534/603, 859, 580

[56] References Cited

U.S. PATENT DOCUMENTS 1,963,133  6/1934  Jordan et al. ............... 534/859
3,524,842  8/1970  Grossmann et al. ............... 534/613

FOREIGN PATENT DOCUMENTS 1923123  11/1970  Germany .
4220388  12/1993  Germany .
8-143435  6/1996  Japan .

Primary Examiner—Paul Lieberman
Assistant Examiner—Caroline D. Liott
Attorney, Agent, or Firm—Whyte Hirschboeck Dudek SC

[57] ABSTRACT

Diazo dyes of the general formula (I)

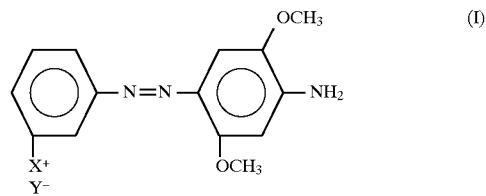

are described where $X^+$ is a quaternary ammonium group and $Y^-$ is a counterbalancing anion. The dyes are useful for coloring hair.

15 Claims, No Drawings

CATIONIC DIAZO DYES FOR THE DYEING OF HAIR

BACKGROUND OF THE INVENTION

The present invention relates to dyes and more particularly to diazo dyes which are suitable for use in hair coloring formulations. The invention also relates to such hair coloring formulations.

BRIEF SUMMARY OF THE INVENTION

According to a first aspect of the present invention there are provided diazo dyes of the general formula (I)

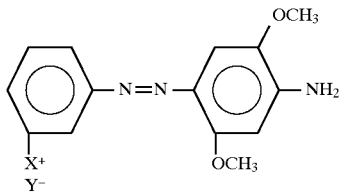

where $X^+$ is a quaternary ammonium group and $Y^-$ is a counterbalancing anion.

A second aspect of the present invention is a hair coloring formulation comprising a dye of formula (I) and a liquid vehicle in which the dye is dissolved.

DETAILED DESCRIPTION OF THE INVENTION

Dyes in accordance with the first aspect of the invention are orange colored and are eminently suitable for use as hair dyes, particularly as semi-permanent hair dyes which will maintain hair coloration for, for example, up to 10 treatments with a shampoo.

Preferred dyes in accordance with the invention are those in which $X^+$ is of the formula —$^+NA_1A_2A_3$ where $A_1$, $A_2$ and $A_3$ are the same or different alkyl groups, preferably of 1 to 4 carbon atoms. It is preferred that at least one (and preferably all) of $A_1$, $A_2$ and $A_3$ are methyl groups.

The counterbalancing anion $Y^-$ may be selected from a number of possibilities, for example halide (e.g. chloride), methosulphate, ethosulphate, or metal based anions. It is particularly preferred that $Y^-$ is a trichlorozincate anion.

Dyes in accordance with the invention may be produced by forming the diazonium salt of an amino of the formula II

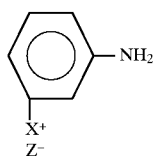

where $Z^-$ is a counterbalancing anion, and coupling the diazonium salt with a compound of the formula III

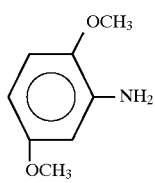

The anion $Z^-$ may be the same as the $Y^-$ anion of the final dye or may be one which is subsequently displaced by a $Y^-$ anion to obtain the final product.

A particularly preferred dye in accordance with the invention is of the formula IV

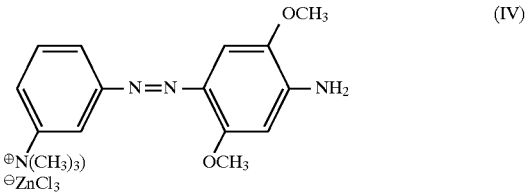

This dye has an excellent orange shade.

As indicated above, the dyes in accordance with the invention are eminently suitable for use as hair dyes. In this respect, the dyes are taken-up well by the hair (due to the presence in the dye of the quaternary ammonium group) and have good fastness in that they will withstand numerous washings of the hair. The dyes are of adequate solubility for use in the vehicles particularly used for hair dye formulations.

Therefore according to a second aspect of the present invention there is provided a hair coloring formulation comprising a dye of formula (I) and a liquid vehicle (e.g. water) in which the dye is dissolved.

The hair coloring formulation will typically contain 0.1% to 1% by weight, e.g. 0.2 to 0.5%, of the dye of formula (I) as well as conventional components of hair coloring formulations, e.g. surfactants, conditioners, thickeners, perfume and/or preservatives.

The formulation may for example be in the form of a liquid, a gel or a mousse. Specific examples of such formulations include a shampoo, a sprayable liquid, a conditioner, a styling mousse, a styling spray, a styling gel, a conditioning styling gel, or a gel mousse.

The preferred dye for use in a hair coloring formulation in accordance with the invention is compound IV above which has a solubility of about 4 g/100 g in water. The compound has good color washout properties and good compatibility with shampoo.

The compound IV may be admixed in varying proportions with other dyes (particularly quaternary dyes) such as available under the Trade Mark ARIANOR to provide a range of colors. Thus, for example, the dye may be admixed with red dyes (which may be conventional red dyes) to provide a range of brown shades. Prior to the development of compound IV, it has not been possible to provide such a range of brown shades in catioilic hair dyes.

The invention will be further described with reference to the following non-limiting Examples.

EXAMPLE 1

This example describes the preparation of 3-[(2,5-dimethoxy-4-amino-phenyl)azo]-N,N,N-trimethylbenzenaminium trichlorzincate (compound IV).

To a solution of 18.6 gm 3-aminophenyl trimethyl ammonium chloride in 300 ml water were add 25 mls of 36% hydrochloric acid. Ice was added to reduce the temperature to 0° C. and the mixture was maintained in an ice bath. A solution of 7 gm sodium nitrite in 50 mls water was then added whilst maintaining the temperature at less than 5° C.

Separately, there was prepared a solution of 15.3 gm of 2,5-dimethoxy aniline in a mixture of 100 ml water and 10 ml 36% hydrochloric acid.

The two solutions where then mixed.

Subsequently, 13.6 gm zinc chloride were added and the product precipitated as a solid by standard methods.

The product was filtered and dried.
The yield was 32 gm of orange colored dye.

EXAMPLE 2

Experiments were undertaken in order to evaluate the hair coloring ability of compound IV in a typical hair coloring shampoo which comprised:

|  | % w/w |
| --- | --- |
| Sodium Cocoamphopropionate | 8.00 |
| Lauryl Betaine | 5.00 |
| Cocamidopropyl Amine Oxide | 5.00 |
| Hydroxy Ethyl Cellulose | 0.25 |
| Preservative | 0.05 |
| Compound (IV) | 0.50 |
| Distilled Water | to 100.00 |

The preservative comprised chloroisothiazolinone and methyl isothiazolinone.

Employing the procedure outlined in steps 1 to 8 below, swatches of human hair were colored using the shampoo formulation and a comparison was made as to the intensity and permanence of the color on the hair.

The procedure was as follows:
1. Swatches of hair weighing 1 g and from the same master batch of human hair, were washed with a commercial detergent solution containing 30% sodium lauryl ether sulphate.
2. The swatches were dried by blotting with tissue paper.
3. The swatches were immersed in the shampoo formulation for 15 minutes. The swatches were agitated during the dyeing time to ensure that all the hairs were coated with the dye.
4. The hair swatches were rinsed in cold tap water until the water ran clear.
5. The swatches were blow dried with a hairdryer and were allowed to equilibrate at ambient temperature for an hour.
6. One swatch was removed from the set.
7. The remaining swatches were shampooed with the shampoo used in Step 1). They were then rinsed and dried as in Steps 4) and 5).
8. Steps 6) and 7) were then repeated to give a series of swatches that has been progressively shampooed.

After coloring, the hair had a bright orange shade.

The sets of colored swatches were ranked by a trained panel of assessors, who ranked them according to their color intensity on a scale of 0 (no color) to 10 (most intense color).

The ranking scores obtained for the color washout by the trained panel of follows:

| Number of Shampoos (N) | Intensity Color Score (I) |
| --- | --- |
| 0 | 8.02 |
| 1 | 5.00 |
| 3 | 3.10 |
| 6 | 1.25 |

A plot of $\log_{10}$ (I) vs (N) was of the form:

$$\text{Log}_{10} (I) = 0.90 - 0.125(N)$$

Thus demonstrating that the rate of color washout was 0.125. This is a typical value for a semi-permanent hair dye and indicates that the dye will maintain hair coloration for up to about 10 shampoos.

EXAMPLE 3

Example 1 was repeated with two different dye systems:

a) Compound IV at 0.25% w/w plus Arianor Sienna Brown (ex Warner Jenkinson) at 0.25% w/w.

b) Compound IV at 0.25% w/w plus Arianor Mahogany (ex Warner Jenkinson) at 0.25% w/w.

After coloring the hair, the shades obtained were a light brown in the case of dye system a) and deep brown in the case of dye system b). The ranking scores obtained for the color washout were as follows:

| Number of Sharpness (N) | Dye system (a) Color Intensity Score (I) | Dye system (b) Color Intensity Score (I) |
| --- | --- | --- |
| 0 | 8.30 | 8.91 |
| 1 | 6.00 | 6.92 |
| 3 | 3.30 | 3.89 |
| 6 | 1.32 | 1.58 |

Analysis of these data gave the following relationships between N and I:

$$\text{Log}_{10} (I) = 0.92 - 0.133(N) \text{ for dye system } (a)$$

and $$\text{Log}_{10} (I) = 0.95 - 0.135(N), \text{ for dye systems } (B)$$

These relationships show that the washout rate of compound IV (0.125) is very similar to the washout rate of compound IV plus Arianor Sienna Brown (0.133) and to the washout rate of compound IV plus Arianor Mahogany (0.135). These similarities are important so that consistency of hair color is maintained during repeated shampoos.

What is claimed is:

1. Diazo dyes of the general formula (I)

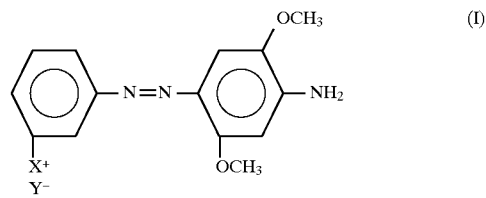

where $X^+$ is a quaternary ammonium group and $Y^-$ is a counterbalancing anion.

2. A dye as claimed in claim 1, wherein $X^+$ is of the formula $+\ ^-NA_1A_2A_3$ where $A_1$, $A_2$ and $A_3$ are the same or different alkyl groups.

3. A dye as claimed in claim 2 wherein $A_1$, $A_2$ and $A_3$ each have 1 to 4 carbon atoms.

4. A dye as claimed in claim 3 wherein $A_1$, $A_2$ and $A_3$ are each methyl groups.

5. A dye as claimed in claim 1 wherein $Y^-$ is halide, methylsulphate, ethylsulphate or a metal based anion.

6. A dye as claimed in claim 5 wherein $Y^-$ is a trichlorozincate anion.

7. A dye of the general formula IV

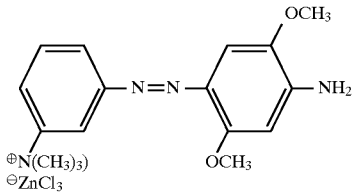 (IV)

8. A method of producing a dye as claimed in claim 1 comprising forming a diazonium salt of an amino of the formula II

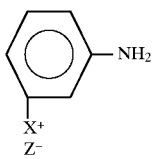 (II)

where $X^+$ is as defined for formula I and $Z^-$ is a counter-balancing anion, and coupling the diazonium salt with a compound of the formula III

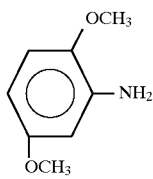 (III)

9. A hair dye formulation comprising a dye as claimed in claim 1 and a liquid vehicle in which the dye is dissolved.

10. A formulation as claimed in claim 9 containing 0.1% to 1% by weight of said dye.

11. A formulation as claimed in claim 10 comprising 0.2 to 0.5% by weight of said dye.

12. A formulation as claimed in claim 9 in the form of a liquid, a gel or a mousse.

13. A formulation as claimed in claim 12 which is a shampoo, a sprayable liquid, a conditioner, a styling mousse, a styling spray, a styling gel, a conditioning styling gel, or a gel mousse.

14. A method of coloring hair comprising treating the hair with a dye as claimed in claim 1.

15. A method of coloring hair comprising treating the hair with a formulation as claimed in claim 9.

* * * * *

UNITED STATES PATENT AND TRADEMARK OFFICE
CERTIFICATE OF CORRECTION

PATENT NO. : 5,879,413
DATED : March 9, 1999
INVENTOR(S) : Roger W. Pengilly; Francis C.P. McLoughlin; Roger G.J.C. Twigg It is certified that error appears in the above-identified patent and that said Letters Patent is hereby corrected as shown below:

Column 1, line 47: Replace "amino" with --amine--.

Column 4, line 56: Replace "+$NA_1A_2A_3$" with -- -$^+NA_1A_2A_3$--

Column 5, line 13: Replace "amino" with --amine--.

Signed and Sealed this

Sixth Day of July, 1999

Q. TODD DICKINSON

Attest:

*Attesting Officer*        *Acting Commissioner of Patents and Trademarks*